United States Patent
Nam et al.

(10) Patent No.: US 10,524,666 B2
(45) Date of Patent: Jan. 7, 2020

(54) WHITE EXCITATION LIGHT GENERATING DEVICE AND WHITE EXCITATION LIGHT GENERATING METHOD

(71) Applicant: INNER RAY, INC., San Ramon, CA (US)

(72) Inventors: Dong Wook Nam, San Ramon, CA (US); Joo Hyung Hong, Suwon-si (KR)

(73) Assignee: Inner Ray, Inc., San Ramon, CA (US)

( * ) Notice: Subject to any disclaimer, the term of this patent is extended or adjusted under 35 U.S.C. 154(b) by 0 days.

(21) Appl. No.: 15/975,032

(22) Filed: May 9, 2018

(65) Prior Publication Data

US 2019/0343391 A1 Nov. 14, 2019

(51) Int. Cl.
*A61B 5/00* (2006.01)
*G01J 3/46* (2006.01)
*G01J 3/44* (2006.01)
*G01J 3/10* (2006.01)

(52) U.S. Cl.
CPC .............. *A61B 5/0071* (2013.01); *G01J 3/10* (2013.01); *G01J 3/4406* (2013.01); *G01J 3/465* (2013.01); *G01J 2003/104* (2013.01); *G01J 2003/468* (2013.01)

(58) Field of Classification Search
CPC ........ A61B 5/0071; G01J 3/10; G01J 3/4406; G01J 3/465; G01J 2003/104; G01J 2003/468
See application file for complete search history.

(56) References Cited

U.S. PATENT DOCUMENTS

| | | | |
|---|---|---|---|
| 7,996,068 B2 * | 8/2011 | Telischak | A61B 5/0071 600/431 |
| 9,743,836 B2 | 8/2017 | Tsubouchi et al. | |
| 2006/0066266 A1 * | 3/2006 | Li Lim | G02F 1/133603 315/291 |
| 2007/0064228 A1 * | 3/2007 | Tartakovsky | G01J 3/10 356/317 |
| 2009/0289200 A1 | 11/2009 | Ishii | |
| 2011/0125028 A1 | 5/2011 | Wood et al. | |

(Continued)

FOREIGN PATENT DOCUMENTS

| | | |
|---|---|---|
| JP | 3487933 | 1/2004 |
| JP | 3568280 | 9/2004 |

(Continued)

*Primary Examiner* — Dominic J Bologna
(74) *Attorney, Agent, or Firm* — Knobbe, Martens, Olson & Bear, LLP (57) ABSTRACT

In general aspect, a white excitation light generating device can include a fluorescent excitation light source that generates fluorescent excitation light, a first light source that generates first monochromatic light of a first wavelength different from a wavelength of the fluorescent excitation light, a second light source that generates second monochromatic light of a second wavelength different from the wavelength of the fluorescent excitation light and the first wavelength, a spectrophoto sensor that measures tristimulus values of at least one of the fluorescent excitation light, the first monochromatic light, and the second monochromatic light, and a controller that adjusts an output of at least one of the fluorescent excitation light source, the first light source, and the second light source on the basis of the measured tristimulus values.

18 Claims, 8 Drawing Sheets

(56) References Cited

U.S. PATENT DOCUMENTS

| | | | |
|---|---|---|---|
| 2012/0259231 A1* | 10/2012 | Tsubouchi | A61B 5/0059 |
| | | | 600/477 |
| 2017/0077363 A1* | 3/2017 | Oh | H01L 33/50 |
| 2017/0079741 A1* | 3/2017 | Makinouchi | A61B 90/36 |
| 2017/0244009 A1* | 8/2017 | Lee | C03C 4/12 |
| 2017/0299792 A1* | 10/2017 | Oh | F21V 9/30 |
| 2018/0000330 A1 | 1/2018 | Tekeuchi et al. | |
| 2018/0024060 A1* | 1/2018 | Rochette | G01N 21/94 |
| | | | 422/69 |

FOREIGN PATENT DOCUMENTS

| | | |
|---|---|---|
| JP | 1999024053 | 11/2004 |
| JP | 2003111716 | 11/2004 |
| JP | 2006180926 | 8/2007 |
| JP | 2006102360 | 10/2007 |
| JP | 5623266 | 11/2014 |
| JP | 5915949 | 5/2016 |
| JP | 6152951 | 6/2017 |
| KR | 101784063 | 10/2017 |
| KR | 101784970 | 10/2017 |
| KR | 1020180006668 | 4/2018 |
| WO | WO2009/052466 | 4/2009 |
| WO | WO2012/003127 | 1/2012 |
| WO | WO2015/103420 | 7/2015 |

\* cited by examiner

WHITE EXCITATION LIGHT GENERATING DEVICE AND WHITE EXCITATION LIGHT GENERATING METHOD

BACKGROUND

Field of the Invention

The invention relates to a white excitation light generating device and a white excitation light generating method.

Description of the Related Art

A fluorescent material administered into a human body can be used to identify a lesion. A lesion can be easily distinguished from neighboring normal tissues by fluorescent light. When a fluorescent material is irradiated with fluorescent excitation light of a specific wavelength, the fluorescent material emits light of a wavelength other than that of the fluorescent excitation light, that is, fluorescent light. Although it depends on a type of a fluorescent material, for example, red or near-infrared light can be used as fluorescent excitation light in an indocyanine green (ICG). An incised portion looks red. Red-based fluorescent excitation light expresses an incised portion in the substantially same excitation light color as a whole. Accordingly, a surgeon familiar with an illumination of white light has difficulty in securing an accurate field of viewing. In order to solve such inconvenience, an incised portion can be irradiated with white light. However, since white light is light of continuous wavelengths, white light may hinder a fluorescent camera from acquiring fluorescent light. Even if an incised portion is additionally irradiated with white light, an incised portion irradiated with excitation light still looks red due to red-based fluorescent excitation light. This phenomenon can occur in a case in which blue-based or green-based fluorescent excitation light is used as well as a case in which red-based fluorescent excitation light is used. That is, the phenomenon in which an incised portion is visually recognized in a color different from the original color due to the excitation light makes surgeon have difficulty in securing an accurate field of view. Additionally applied white light can overlap the wavelength of fluorescent light and hinder acquisition of fluorescent light by the fluorescent camera.

SUMMARY

In general aspect, a white excitation light generating device can include a fluorescent excitation light source that generates fluorescent excitation light, a first light source that generates first monochromatic light of a first wavelength different from a wavelength of the fluorescent excitation light, a second light source that generates second monochromatic light of a second wavelength different from the wavelength of the fluorescent excitation light and the first wavelength, a spectrophoto sensor that measures tristimulus values of at least one of the fluorescent excitation light, the first monochromatic light, and the second monochromatic light, and a controller that adjusts an output of at least one of the fluorescent excitation light source, the first light source, and the second light source on the basis of the measured tristimulus values. Mixed light in which the monochromatic light of the first wavelength, the monochromatic light of the second wavelength, and the fluorescent excitation light are mixed can be white light.

Implementations of the white excitation light generating device in general aspect can include one or more of the following features.

The controller can include a microprocessor that calculates chromaticity values of the fluorescent excitation light, the first monochromatic light, and the second monochromatic light using the measured tristimulus values, calculates illuminance adjustment values of the first monochromatic light and the second monochromatic light using the calculated chromaticity values, and adjusts an output of at least one of the first light source and the second light source on the basis of the calculated illuminance adjustment values.

The illuminance adjustment values of the first monochromatic light and the second monochromatic light are values for adjusting chromaticity values of the mixed light to chromaticity values of white light.

The white excitation light generating device can further include an illuminance sensor that measures an illuminance value of at least one of the fluorescent excitation light, the first monochromatic light, and the second monochromatic light. The controller calculates chromaticity values of the fluorescent excitation light, the first monochromatic light, and the second monochromatic light using the measured tristimulus values, calculates illuminance adjustment values of the first monochromatic light and the second monochromatic light using the measured illuminance value and the calculated chromaticity values of the fluorescent excitation light, and adjusts an output of at least one of the first light source and the second light source on the basis of the calculated illuminance adjustment values.

The white excitation light generating device can further include an illuminance sensor that measures an illuminance value of at least one of the fluorescent excitation light, the first monochromatic light, and the second monochromatic light. The controller calculates chromaticity values of the fluorescent excitation light, the first monochromatic light, and the second monochromatic light using the measured tristimulus values, calculates illuminance adjustment values of the second monochromatic light and the fluorescent excitation light using the measured illuminance value and the calculated chromaticity values of the first monochromatic light, and adjusts an output of at least one of the first light source and the fluorescent excitation light source on the basis of the calculated illuminance adjustment values.

The fluorescent excitation light source, the first light source, and the second light source are narrow-band LEDs, the first wavelength belongs to a blue band, the second wavelength belongs to a green band, and the wavelength of the fluorescent excitation light belongs to a near-infrared band. For example, the wavelength of the first monochromatic light is 460 nm, the wavelength of the second monochromatic light is 540 nm, and/or the wavelength of the fluorescent excitation light is 780 nm.

In another general aspect, a white excitation light generating device can include a fluorescent excitation light source that generates fluorescent excitation light, a first light source that generates first monochromatic light of a first wavelength different from a wavelength of the fluorescent excitation light, a second light source that generates second monochromatic light of a second wavelength different from the wavelength of the fluorescent excitation light and the first wavelength, an illuminance sensor that measures an illuminance value of at least one of the fluorescent excitation light, the first monochromatic light, and the second monochromatic light and a controller that adjusts an output of at least one of the fluorescent excitation light source, the first light source, and the second light source on the basis of the measured illuminance values. Mixed light in which the monochromatic light of the first wavelength, the monochromatic light of the second wavelength, and the fluorescent excitation light are mixed can be white light.

Implementations of the white excitation light generating device in another aspect can include one or more of the following features.

The white excitation light generating device further includes a memory that stores chromaticity values of the fluorescent excitation light, the first monochromatic light, and the second monochromatic light. The controller includes a microprocessor that calculates the illuminance values of the first monochromatic light and the second monochromatic light using the chromaticity values of the fluorescent excitation light, the first monochromatic light, and the second monochromatic light, compares the calculated illuminance values with the measured illuminance values to calculate illuminance adjustment values, and adjusts an output of the first light source and the second light source on the basis of the calculated illuminance adjustment values.

The white excitation light generating device further includes a memory that stores calculated illuminance values of the fluorescent excitation light, the first monochromatic light, and the second monochromatic light which are mixed into white light. The controller includes a microprocessor that compares the calculated illuminance values with the measured illuminance values to calculate illuminance adjustment values and adjusts an output of the first light source and the second light source on the basis of the calculated illuminance adjustment values.

In still another general aspect, a white excitation light generating method can include generating fluorescent excitation light, first monochromatic light of a first wavelength, and second monochromatic light of a second wavelength, causing a spectrophoto sensor to measure tristimulus values of at least one of the fluorescent excitation light, the first monochromatic light, and the second monochromatic light, and causing a controller to adjust illuminance values of at least one of the fluorescent excitation light, the first monochromatic light, and the second monochromatic light on the basis of the measured tristimulus values. Mixed light in which the monochromatic light of the first wavelength, the monochromatic light of the second wavelength, and the fluorescent excitation light are mixed is white light.

Implementations of the white excitation light generating method can include one or more of the following features.

The causing the controller to adjust an illuminance value of at least one of the fluorescent excitation light, the first monochromatic light, and the second monochromatic light on the basis of the measured tristimulus value includes calculating chromaticity values of the fluorescent excitation light, the first monochromatic light, and the second monochromatic light using the measured tristimulus value, calculating illuminance adjustment values of the first monochromatic light and the second monochromatic light using the calculated chromaticity values, and adjusting outputs of a first light source that generates the first monochromatic light and a second light source that generates the second monochromatic light on the basis of the calculated illuminance adjustment value.

The white excitation light generating method further includes causing an illuminance sensor to measure an illuminance value of at least one of the fluorescent excitation light, the first monochromatic light, and the second monochromatic light. The causing the controller to adjust the illuminance value of at least one of the fluorescent excitation light, the first monochromatic light, and the second monochromatic light on the basis of the measured tristimulus value includes calculating chromaticity values of the fluorescent excitation light, the first monochromatic light, and the second monochromatic light using the measured tristimulus value, calculating illuminance values of the first monochromatic light and the second monochromatic light using the measured illuminance value and the calculated chromaticity values of the fluorescent excitation light, comparing the calculated illuminance values of the first monochromatic light and the second monochromatic light with the measured illuminance values to calculate illuminance adjustment values, and adjusting outputs of a first light source that generates the first monochromatic light and a second light source that generates the second monochromatic light on the basis of the calculated illuminance adjustment values.

The white excitation light generating method further includes causing an illuminance sensor to measure an illuminance value of at least one of the fluorescent excitation light, the first monochromatic light, and the second monochromatic light. The causing the controller to adjust the illuminance value of at least one of the fluorescent excitation light, the first monochromatic light, and the second monochromatic light on the basis of the measured tristimulus value includes calculating chromaticity values of the fluorescent excitation light using the measured tristimulus value, calculating an illuminance value of the fluorescent excitation light and the second monochromatic light using the measured illuminance value and the calculated chromaticity values of the first monochromatic light, comparing the calculated illuminance values of the fluorescent excitation light and the second monochromatic light with the measured illuminance values to calculate illuminance adjustment values, and adjusting outputs of a fluorescent excitation light source that generates the fluorescent excitation light and a second light source that generates the second monochromatic light on the basis of the calculated illuminance adjustment values.

The spectrophoto sensor sequentially measures of the tristimulus values of the fluorescent excitation light, the first monochromatic light, and the second monochromatic light.

The first wavelength belongs to a blue band, the second wavelength belongs to a green band, and the wavelength of the fluorescent excitation light belongs to a near-infrared band.

BRIEF DESCRIPTION OF THE DRAWINGS

Hereinafter, embodiments of the invention will be described with reference to the accompanying drawings. For the purpose of easy understanding of the invention, the same elements will be referred to by the same reference signs. Configurations illustrated in the drawings are examples for describing the invention, and do not restrict the scope of the invention. Particularly, in the drawings, some elements are slightly exaggerated for the purpose of easy understanding of the invention. Since the drawings are used to easily understand the invention, it should be noted that widths, thicknesses, and the like of elements illustrated in the drawings might change at the time of actual implementation thereof. On the other hand, the same elements in the following detailed description of the invention will be referred to by the same reference signs, wherein.

DETAILED DESCRIPTION OF EMBODIMENTS

The invention can be modified and be embodied in various forms, and specific embodiments thereof will be illustrated and described below. However, the embodiments are not intended to limit the invention, but it should be understood that the invention includes all modifications, equivalents, and replacements belonging to the concept and the technical scope of the invention.

Terms "first," "second," and the like can be used to describe various elements, but the elements should not be limited to the terms. The terms are used only to distinguish an element from another.

The terms used in the following description are intended to merely describe specific embodiments, but not intended to limit the invention. An expression of the singular number includes an expression of the plural number, so long as it is clearly read differently. The terms such as "comprise", "include" and "have" are intended to indicate that features, numbers, steps, operations, elements, components, or combinations thereof used in the following description exist and it should thus be understood that the possibility of existence or addition of one or more other different features, numbers, steps, operations, elements, components, or combinations thereof is not excluded.

Hereinafter, embodiments of the invention will be described in detail with reference to the accompanying drawings.

Figure 1:
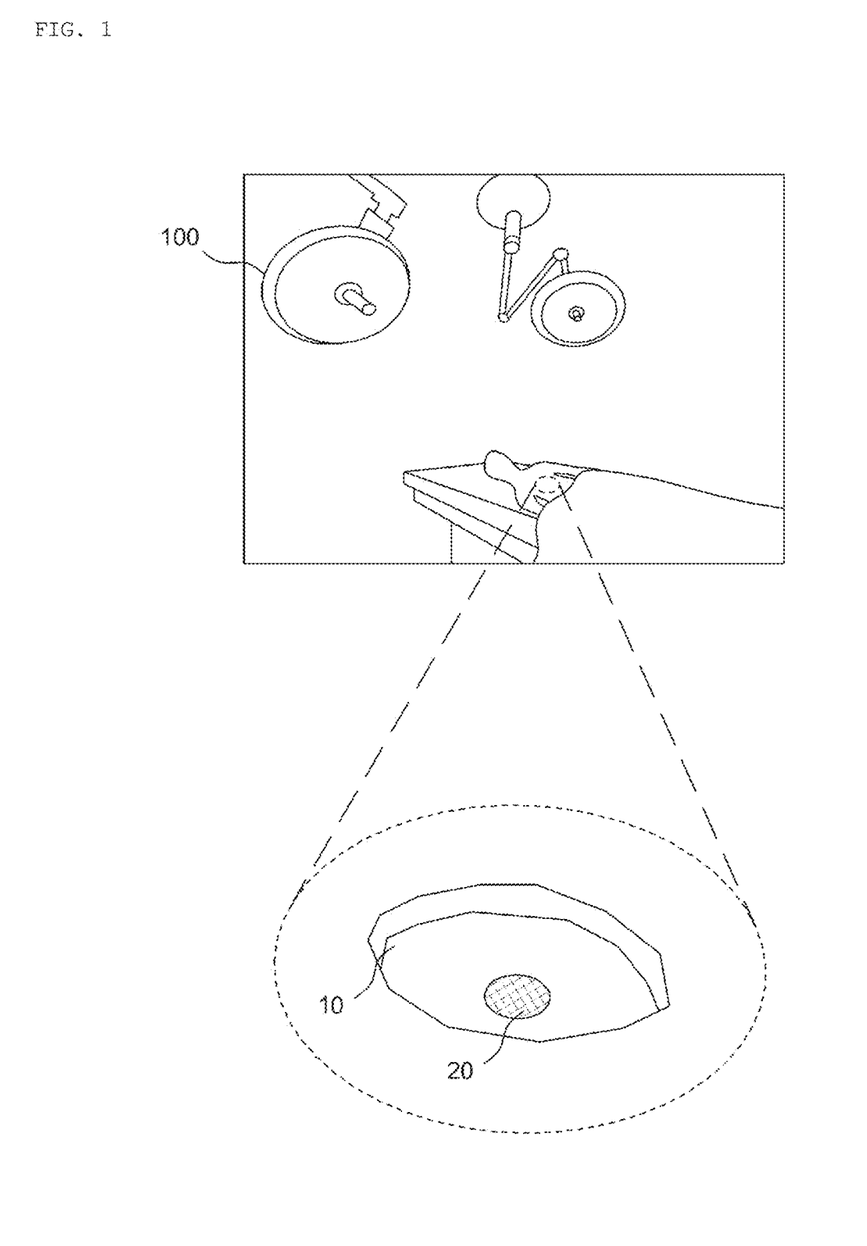
FIG. 1 is a diagram schematically illustrating an operating room in which a white excitation light generating device is installed.

FIG. 1 is a diagram schematically illustrating an operating room in which a white excitation light generating device is installed.

A white excitation light generating device 100 can be implemented as an illumination device of an operating room. The white excitation light generating device 100 is installed near an operating table and irradiates an incised portion 10 with white excitation light. A surgeon or an assistant can observe the incised portion with bare eyes using light reflected from the incised portion 10. Light reflected from the incised portion 10 includes fluorescent light 20 generated from a fluorescent material. A fluorescent material injected into a human body before operation is excited by white excitation light and emits fluorescent light 20. In comparison with a case in which the incised portion is irradiated with monochromatic fluorescent excitation light, for example, blue, green, or red fluorescent excitation light, the incised portion 10 is recognized as the original color using the white excitation light. Accordingly, a surgeon can easily identify a lesion which is naturally expressed in the original color in the incised portion 10. On the other hand, when the wavelength of the fluorescent light 20 belongs to a visible light wavelength band, a surgeon can easily identify the incised portion 10 and can additionally acquire a fluorescent image while keeping familiarity with an existing operating system, which is helpful to a more accurate operation.

White excitation light can be generated by mixing two or more monochromatic light components and fluorescent excitation light. The wavelength bands of the two or more monochromatic light components are different from the wavelength band of the fluorescent excitation light. The wavelength band of monochromatic light can be selected in consideration of the wavelength band of fluorescent light 20. In general, white light is continuous light, but fluorescent light 20 is monochromatic light belonging to a specific wavelength band. Particularly, the intensity of fluorescent light 20 is relatively smaller than that of white light. Accordingly, when the incised portion 10 is irradiated with white light, a surgeon has difficulty in identifying fluorescent light 20 which is relatively weak. For example, the wavelength bands of two or more monochromatic light components which are used to realize white excitation light can be determined such that they are different from the wavelength band of fluorescent light 20 which is determined depending on a type of a fluorescent material. For example, a 5-Aminolevulinic Acid (5-ALA) is excited by fluorescent excitation light of about 400 nm and emits fluorescent light 20 having a peak value at about 635 nm. An Indocyanine green (ICG) is excited by fluorescent excitation light of about 750 nm to about 800 nm and emits fluorescent light 20 having a peak value at about 845 nm. For example, the wavelength bands of the monochromatic light and the fluorescent excitation light may partially overlap the wavelength band of the fluorescent light 20. Even if the wavelength bands overlap, the wavelength bands can be determined such that the peak values thereof are different from each other.

Illuminance values of two or more monochromatic light components and fluorescent excitation light can be adjusted to be white light by mixing. For example, a wavelength of first monochromatic light may belong to a blue band, a wavelength of second monochromatic light may belong to a green band, a wavelength of fluorescent excitation light may belong to a near-infrared band. For example, the wavelength of the first monochromatic light may belong to a green band, the wavelength of the second monochromatic light may belong to a red band, the wavelength of the fluorescent excitation light may belong to a blue band. For example, the wavelength of the first monochromatic light may belong to a blue band, the wavelength of the second monochromatic light may belong to a red band, the wavelength of the fluorescent excitation light may belong to a green band. For example, the illuminance values of the first monochromatic light and the second monochromatic light can be adjusted with respect to the illuminance value of the fluorescent excitation light. For example, the illuminance values of the fluorescent excitation light and the second monochromatic light may be adjusted with respect to the illuminance value of the first monochromatic light.

Figure 2:
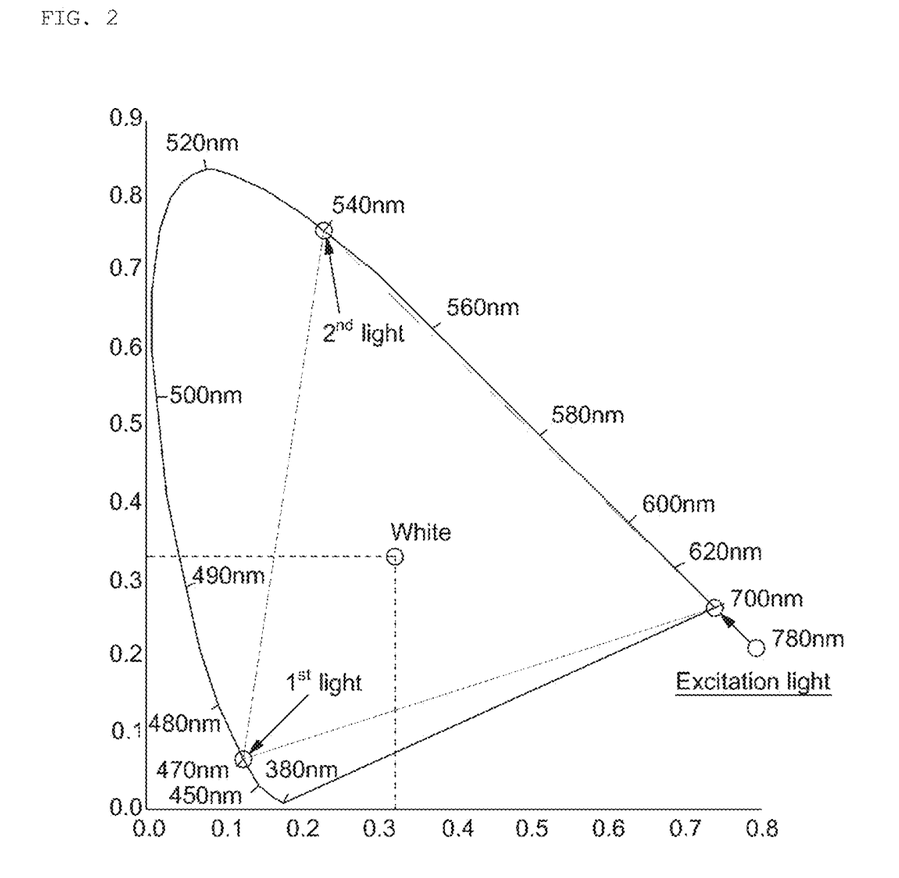
FIG. 2 is a diagram schematically illustrating a principle of generating white excitation light using a CIExyY color space chromaticity diagram.

FIG. 2 is a diagram schematically illustrating a principle of generating white excitation light using a CIE 1931 color space chromaticity diagram.

All colors which are recognized by a human being can be digitized. A CIExyY color space chromaticity diagram which is one of various color spaces in which colors are digitized expresses chromaticity values in x and y coordinates. The CIExyY color space chromaticity diagram is described below as an example of a color space, but this is only an example and is not intended to exclude other color spaces. In the CIExyY color space chromaticity diagram, x and y chromaticity values of monochromatic light are distributes in an edge curve of the color space chromaticity diagram. In the CIExyY color space chromaticity diagram, a person recognizes white light when x and y are about ⅓ and about ⅓. When three points are designated in the CIExyY color space chromaticity diagram, a color inside a triangle with the three points as vertexes can be expressed by mixing colors corresponding to the three points. Accordingly, by appropriately selecting two monochromatic light components and one fluorescent excitation light component and adjusting illuminance values thereof, white excitation light can be generated.

Illuminance values of first monochromatic light, second monochromatic light, and fluorescent excitation light which generate white excitation light by mixing are determined as follows. First, chromaticity values x, y, and z of the first monochromatic light, the second monochromatic light, and the fluorescent excitation light are calculated. The chromaticity values x, y, and z can be expressed by X, Y, and Z as described below.

$$x = \frac{X}{X+Y+Z}, y = \frac{Y}{X+Y+Z}, z = \frac{Z}{X+Y+Z} \quad (1)$$

Here, the fluorescent excitation light has chromaticity values of $x_r$ and $y_r$ and an illuminance value of $Y_r$, the first monochromatic light has chromaticity values of $x_b$ and $y_b$ and an illuminance value of $Y_b$, and the second monochromatic light has chromaticity values of $x_g$ and $y_g$ and an illuminance value of $Y_g$. The chromaticity values $x_r$, $y_r$, $x_b$, $y_b$, $x_g$, and $y_g$ are constants which can be acquired from measured tristimulus values or the CIExyY color space chromaticity diagram. The chromaticity values of white excitation light is ⅓ and ⅓ and can be expressed as follows.

$$\frac{1}{3} = x_r \times \frac{Y_r}{(Y_r + Y_b + Y_g)} \quad (2)$$

$$\frac{1}{3} = y_r \times \frac{Y_r}{(Y_r + Y_b + Y_g)} \quad (3)$$

Equations (2) and (3) can be expressed as follows.

$$(3x_r-1)Y_r+(3x_g-1)Y_g+(3x_b-1)Y_b=0 \quad (4)$$

$$(3y_r-1)Y_r+(3y_g-1)Y_g+(3b-1)Y_b=0 \quad (5)$$

Here, the following definitions are determined to simplify calculations.

$$3x_r-1=x_1 \quad (6)$$

$$3x_g-1=x_2 \quad (7)$$

$$3x_b-1=x_3 \quad (8)$$

$$3y_r-1=y_1 \quad (9)$$

$$3y_g-1=y_2 \quad (10)$$

$$3y_b-1=y_3 \quad (11)$$

Then, Equations (4) and (5) can be expressed using $Y_b$ and $Y_g$ as follows.

$$Y_b = \frac{x_1 y_2 - x_2 y_1}{x_2 y_3 - x_3 y_2} Y_r \quad (12)$$

$$Y_g = \frac{-x_3 y_b - x_1 Y_r}{x_2} \quad (13)$$

The calculated illuminance values $Y_r$, $Y_b$, and $Y_g$ are illuminance which is required for generating white excitation light. The calculated illuminance values $Y_r$, $Y_b$, and $Y_g$ may not be equal to the measured illuminance values $Y'_r$, $Y'_b$, and $Y'_g$. Accordingly, outputs of light sources are adjusted such that proportions between the measured illuminance values $Y'_r$, $Y'_b$, and $Y'_g$ are equal to proportions between the calculated illuminance values $Y_r$, $Y_b$, and $Y_g$. Accordingly, mixed light of the fluorescent excitation light, the first monochromatic light, and the second monochromatic light is white excitation light.

Figure 3:
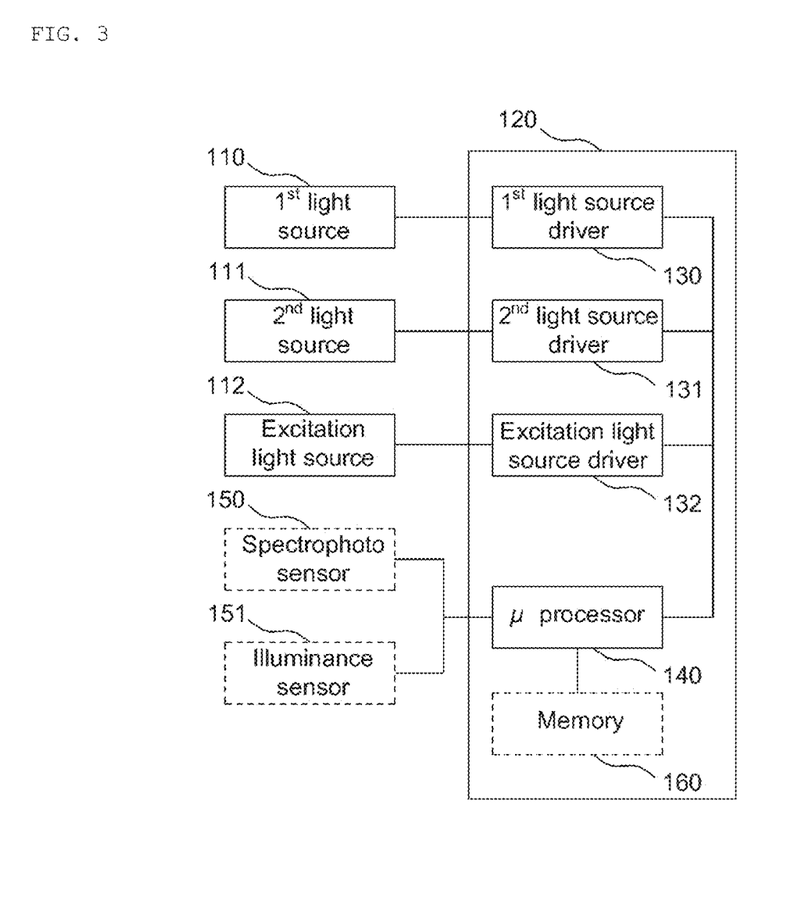
FIG. 3 is a diagram schematically illustrating a configuration of the white excitation light generating device illustrated in FIG. 1.

FIG. 3 is a diagram schematically illustrating a configuration of the white excitation light generating device illustrated in FIG. 1.

Referring to FIG. 3, the white excitation light generating device 100 includes a first light source 110, a second light source 111, a fluorescent excitation light source 112, and a controller 120. The white excitation light generating device 100 may further include a spectrophoto sensor 150. On the other hand, the white excitation light generating device 100 may further include an illuminance sensor 151.

The first light source 110 generates first monochromatic light in a first wavelength band, and the second light source 111 generates second monochromatic light in a second wavelength band. The fluorescent excitation light source 112 generates fluorescent excitation light in a third wavelength band. For example, the wavelength of the first monochromatic light and the second monochromatic light belong to a visible light wavelength band of 400 nm to 700 nm, and the wavelength of the fluorescent light belongs to a red wavelength band in which fluorescent light is emitted by exciting a fluorescent material or a near-infrared wavelength band of equal to or greater than 700 nm. For example, the first monochromatic light, the second monochromatic light, and the fluorescent excitation light may belong to the visible light wavelength band. That is, the wavelength band of the fluorescent excitation light can be determined depending on a wavelength which is required for exciting a fluorescent material administered to a human body.

The first wavelength band, the second wavelength band, the third wavelength band, and the wavelength band of fluorescent light are different from each other. That is, the first wavelength band, the second wavelength band, the third wavelength band, and the wavelength band of fluorescent light do not overlap each other or do not match each other in peak value even if they partially overlap each other. In order to effectively separate the first wavelength band, the second wavelength band, the third wavelength band, and the wavelength band of fluorescent light, the first light source 110, the second light source 111, and the fluorescent excitation light source 112 may be, for example, narrow-band light emitting diodes.

The controller 120 controls outputs of the first light source 110, the second light source 111, and the fluorescent excitation light source 112. The controller 120 includes a first light source driver 130 that drives the first light source 110, a second light source driver 131 that drives the second light source 111, a fluorescent excitation light source driver 132 that drives the fluorescent excitation light source 112, and a microprocessor 140 that controls the light source drivers.

The first light source driver 130, the second light source driver 131, and the fluorescent excitation light source driver 132 adjust the outputs in accordance with control signals from the microprocessor 140. Accordingly, the illuminance value of at least one of the first monochromatic light, the second monochromatic light, and the fluorescent excitation light can be adjusted. The first light source driver 130, the second light source driver 131, and the fluorescent excitation light source driver 132 may be, for example, light emitting diode drivers that are driven with a DC voltage or are driven with an AC voltage.

The microprocessor 140 controls the output of at least one of the first light source 110, the second light source 111, and the fluorescent excitation light source 112 via the first light source driver 130, the second light source driver 131, and the fluorescent excitation light source driver 132.

For example, the chromaticity values of the first monochromatic light, the second monochromatic light, and the fluorescent excitation light can be acquired by the spectrophoto sensor 150. The microprocessor 140 sets the illuminance values with one of the first monochromatic light, the second monochromatic light, and the fluorescent excitation light as a reference. The illuminance values of the other light components can be calculated as a ratio to the illuminance value of the reference light component. The microprocessor 140 determines an illuminance adjustment value on the basis of the calculated illuminance ratios. The illuminance adjustment value is a control signal for increasing or decreasing an output of a light source.

For example, the chromaticity values and the illuminance values of the first monochromatic light, the second monochromatic light, and the fluorescent excitation light can be acquired using the spectrophoto sensor 150 and the illuminance sensor 151. The spectrophoto sensor 150 measures tristimulus values of the first monochromatic light, the second monochromatic light, and/or the fluorescent excitation light and the illuminance sensor 151 measures an illuminance values of the first monochromatic light, the second monochromatic light, and/or the fluorescent excitation light. The microprocessor 140 calculates the chromaticity values from the tristimulus value of at least one of the first monochromatic light, the second monochromatic light, and the fluorescent excitation light which is measured by the spectrophoto sensor 150. The calculated chromaticity values are used to calculate the illuminance values of the first monochromatic light, the second monochromatic light, and the fluorescent excitation light which can generate white light by mixing using the equations described with reference to FIG. 2. The microprocessor 140 delivers a control signal for adjusting the output of at least one of the first light source 110, the second light source 111, and the fluorescent excitation light source 112 on the basis of the calculated chromaticity values to the first light source driver 130, the second light source driver 131, and the fluorescent excitation light source driver 132. Here, the microprocessor 140 can adjust at least one of the outputs of the first light source 110 and the second light source 111 with the output of the fluorescent excitation light source 112 as a reference. Similarly, the microprocessor 140 can adjust at least one of the outputs of the second light source 111 and the fluorescent excitation light source 112 with the output of the first light source 110 as a reference. The microprocessor 140 compares the measured illuminance values with the calculated illuminance values and determines the illuminance adjustment value.

For example, the chromaticity values of the first monochromatic light, the second monochromatic light, and the fluorescent excitation light may be stored in the memory 160. Since the first wavelength band, the second wavelength band, and the third wavelength band are determined in advance, the chromaticity values can be acquired from the CIExyY color space chromaticity diagram. The microprocessor 140 delivers the illuminance adjustment value for adjusting the output of at least one of the first light source 110, the second light source 111, and the fluorescent excitation light source 112 on the basis of the stored chromaticity values and the illuminance values measured by the illuminance sensor 151 to the first light source driver 130, the second light source driver 131, and the fluorescent excitation light source driver 132.

Figure 4:
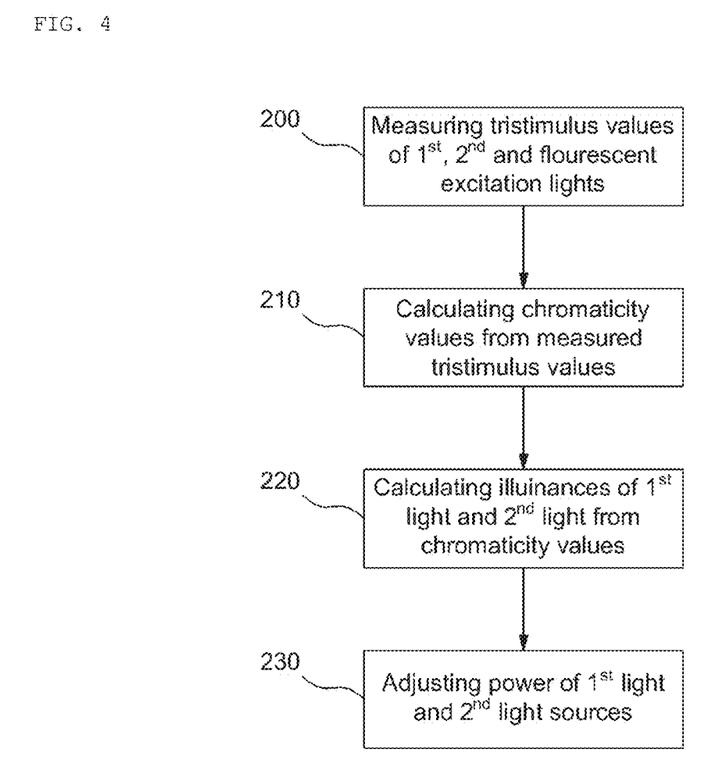
FIG. 4 is a flowchart schematically illustrating operations of the white excitation light generating device illustrated in FIG. 3.

FIG. 4 is a flowchart schematically illustrating operations of the white excitation light generating device illustrated in FIG. 3.

Referring to FIG. 4, in Step 200, the tristimulus value of at least one of the first monochromatic light, the second monochromatic light, and the fluorescent excitation light are measured. The spectrophoto sensor 150 can simultaneously or sequentially the tristimulus values of the first monochromatic light, the second monochromatic light, and/or the fluorescent excitation light. When the tristimulus values are sequentially measured, the microprocessor 140 can sequentially turn on and turn off or can sequentially turn on the first light source 110, the second light source 111, and the fluorescent excitation light source 112. The measured tristimulus values can be stored in the memory 160.

In Step 210, the chromaticity values are calculated using the measured tristimulus values. The microprocessor 140 calculates the chromaticity values of at least one of the first monochromatic light, the second monochromatic light, and the fluorescent excitation light using the measured tristimulus values. The calculated chromaticity values can be stored in the memory 160.

For example, Steps 200 and 210 can be performed whenever the white excitation light generating device 100 is driven. The wavelength bands may shift due to an influence of an ambient environment (for example, temperature, humidity, and ambient light), a deviation in wavelength which may occur between the same light sources, and/or aging of the light sources 110, 111, and 112. When the white excitation light generating device 100 is driven in this situation, the white excitation light generating device 100 can measure the chromaticity values whenever being driven. For example, Steps 200 and 210 may be performed once at the first time such that the chromaticity values of the first monochromatic light, the second monochromatic light, and the fluorescent excitation light may be stored in the memory 160, and then may not be performed when being next driven or may be performed when a predetermined driving time elapses. For example, when the chromaticity values of the first monochromatic light, the second monochromatic light, and the fluorescent excitation light are stored in the memory 160 in advance, Steps 200 and 210 may be omitted. As described above, the wavelength bands of the first monochromatic light, the second monochromatic light, and the fluorescent excitation light can be determined in advance. When the wavelength bands are determined, the chromaticity values of the first monochromatic light, the second monochromatic light, and the fluorescent excitation light are constants which can be acquired from the CIExyY color space chromaticity diagram.

In Step 220, the illuminance values for generating white excitation light are determined. The microprocessor 140 calculates the illuminance value of at least one of the first monochromatic light, the second monochromatic light, and the fluorescent excitation light using the chromaticity values of the first monochromatic light, the second monochromatic light, and the fluorescent excitation light. For example, the microprocessor 140 sets the illuminance value of one of the first monochromatic light, the second monochromatic light, and the fluorescent excitation light as a reference and calculates ratios of the other illuminance values to the illuminance value set as a reference. The microprocessor 140 delivers the illuminance adjustment value based on the calculated illuminance ratios to the first light source driver 130, the second light source driver 131, and the fluorescent excitation light source driver 132. For example, the microprocessor 140 sets one of the measured illuminance values of the first monochromatic light, the second monochromatic light, and the fluorescent excitation light as a reference and calculates the other illuminance values. The microprocessor 140 compares the calculated illuminance values with the measured illuminance values and delivers the illuminance adjustment value increasing or decreasing the outputs by the difference therebetween to the first light source driver 130, the second light source driver 131, and the fluorescent excitation light source driver 132.

In Step 230, the illuminance value of at least one of the first monochromatic light, the second monochromatic light, and the fluorescent excitation light is adjusted. At least one of the first light source driver 130, the second light source driver 131, and the fluorescent excitation light source driver 132 increases or decreases the output of the corresponding light source on the basis of the illuminance adjustment value.

Figure 5:
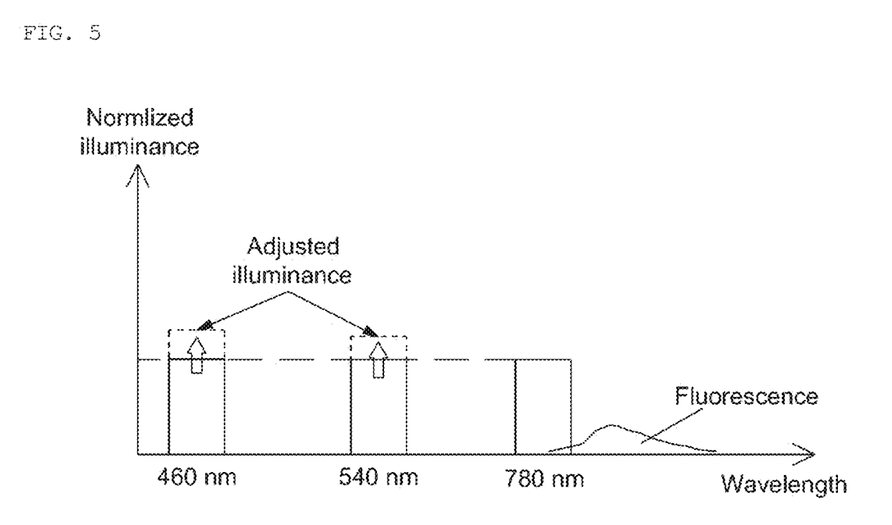
FIG. 5 is a diagram schematically illustrating a method of adjusting illuminance of monochromatic light to generate white excitation light.
Figure 6:
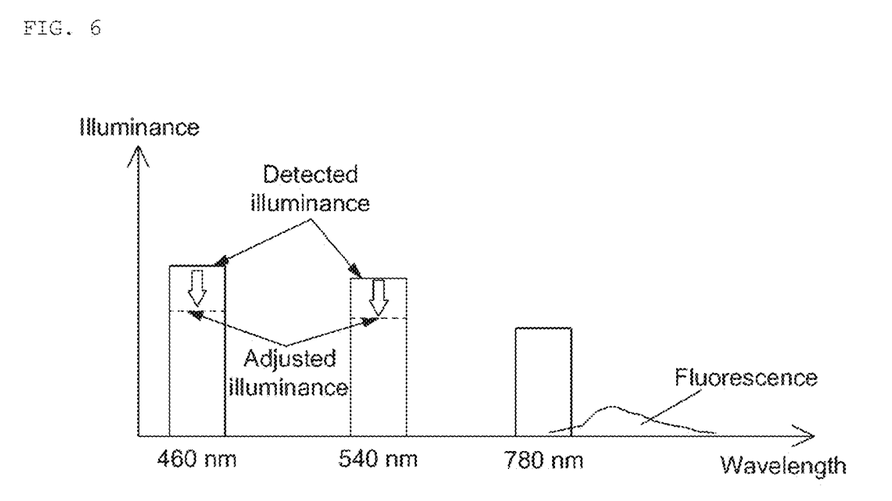
FIG. 6 is a diagram schematically illustrating a method of adjusting illuminance of monochromatic light using measured illuminance.

FIG. 5 is a diagram schematically illustrating a method of adjusting illuminance values of monochromatic light components to generate white excitation light. FIG. 6 is a diagram schematically illustrating a method of adjusting illuminance values of monochromatic light components using measured illuminance values.

Referring to FIGS. 5 and 6 along with FIG. 2, the first monochromatic light has a wavelength of about 460 nm which belongs to a blue band, the second monochromatic light has a wavelength of about 540 nm which belongs to a green band, and the fluorescent excitation light has a wavelength of about 780 nm which belongs to a near-infrared band. Referring to the CIExyY color space chromaticity diagram, and the chromaticity values x and y of light of about 460 nm are about 0.14 and about 0.025, the chromaticity values x and y of light of about 540 nm are about 0.22 and about 0.75. The chromaticity values x and y of light of about 780 nm are similar to those of light of about 700 nm which is in a red wavelength band and are about 0.174 and about 0.26. In order to make mixed light in which the first monochromatic light, the second monochromatic light, and the fluorescent excitation light be white light, the chromaticity values x and y of mixed light have to be about ⅓ and ⅓. The following expressions are obtained by setting the illuminance value of the fluorescent excitation light to 1 and substituting the illuminance value into a general relational expression of chromaticity and illuminance.

$$\text{Mixed } x = \frac{1}{3} = \frac{0.74}{(1+Y_1+Y_2)} + \frac{0.22}{(1+Y_1+Y_2)} + \frac{0.14}{(1+Y_1+Y_2)} \quad (13)$$

$$\text{Mixed } y = \frac{1}{3} = \frac{0.26}{(1+Y_1+Y_2)} + \frac{0.75}{(1+Y_1+Y_2)} + \frac{0.025}{(1+Y_1+Y_2)} \quad (14)$$

Here, $Y_1$ denotes the illuminance value of the first monochromatic light, and $Y_2$ denotes the illuminance value of the second monochromatic light. $Y_1$ of about 1.395 and $Y_2$ of about 1.208 are obtained by solving Equations (13) and (14).

Referring to FIG. 5, the outputs of the first light source 110, the second light source 111, and the fluorescent excitation light source 112 are substantially equal to each other, and thus the illuminance values of the first monochromatic light, the second monochromatic light, and the fluorescent excitation light are substantially equal to each other. However, the wavelength bands thereof do not overlap each other. Particularly, the wavelengths thereof may be less than the wavelength of fluorescent light. As described above, the wavelength of fluorescent light may vary depending on the type of the fluorescent material. Accordingly, the wavelength band of the fluorescent light does not have to be greater than the wavelengths of the first monochromatic light, the second monochromatic light, and the fluorescent excitation light. The ratio of the illuminance values calculated using Equations (13) and (14) is 1.395:1.208:1. Accordingly, the microprocessor 140 delivers a first illuminance adjustment value for increasing the illuminance value of the first monochromatic light by 39.5% to the first light source driver 130 and delivers a second illuminance adjustment value for increasing the illuminance value of the second monochromatic light by 20.8% to the second light source driver 131.

Referring to FIG. 6, the outputs of the first light source 110, the second light source 111, and the fluorescent excitation light source 112 are not substantially equal to each other. In the example illustrated in FIG. 6, the illuminance values of the first monochromatic light and the second monochromatic light are greater than illuminance values which are suitable for generating white excitation light. Accordingly, in order to generate white excitation light, the illuminance values of the first monochromatic light, the second monochromatic light, and the fluorescent excitation light are measured. The microprocessor 140 sets the illuminance value of the fluorescent excitation light as a reference and calculates the illuminance values of the first monochromatic light and the second monochromatic light on the basis of the calculated illuminance ratio. On the basis of the differences between the calculated illuminance values and the measured illuminance values, the microprocessor 140 delivers a first illuminance adjustment value for decreasing the illuminance value of the first monochromatic light to the first light source driver 130 and delivers a second illuminance adjustment value for decreasing the illuminance value of the second monochromatic light to the second light source driver 131.

An example in which the illuminance value of the fluorescent excitation light is set as a reference and the illuminance values of the first monochromatic light and the second monochromatic light are adjusted has been described above. For example, the other illuminance values may be adjusted with the illuminance value of the first monochromatic light or the second monochromatic light as a reference.

Figure 7:
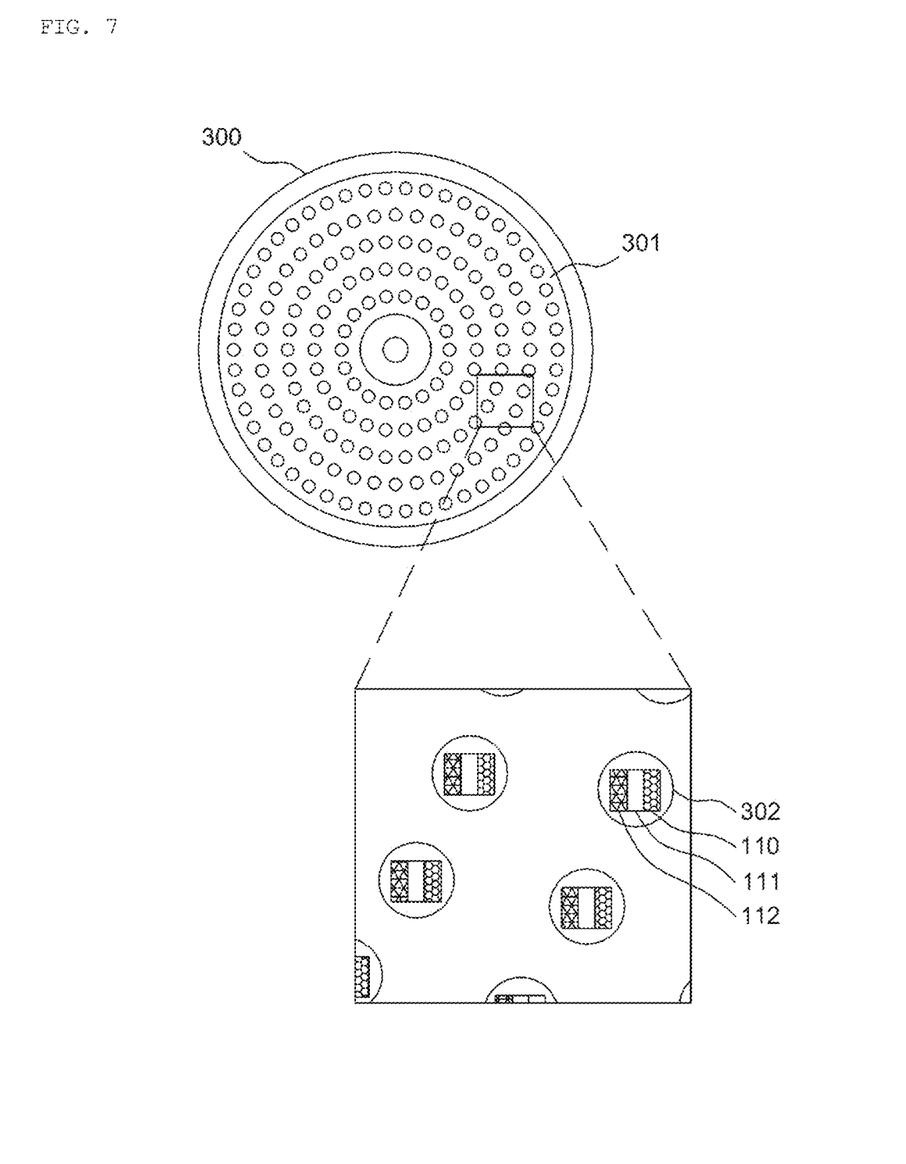
FIG. 7 is a diagram schematically illustrating an arrangement of light sources in a white excitation light generating device which is implemented as an illumination of an operating room.

FIG. 7 is a diagram schematically illustrating an arrangement of light sources in a white excitation light generating device which is implemented as an illumination of an operating room.

The white excitation light generating device 100 may be an illumination device 300 of an operating room. The operating-room illumination device 300 is installed near an operating table. The operating-room illumination device 300 has a semispherical shape or a flat panel shape and the light sources are disposed on a curved surface or a planar surface facing an operating table. The light sources may be separated from each other and be arranged on the curved surface or the planar surface, or may be grouped into pairs and be arranged on the curved surface or the planar surface. FIG. 7 illustrates a structure in which the first light source 110, the second light source 111, and the fluorescent excitation light source 112 are grouped in pairs and are arranged on the planar surface. A plurality of light source pairs 110, 111, and 112 are separated from each other and arranged on a planar surface 301 facing an operating table in the operating-room illumination device. A plurality of areas 302 in which the light sources 110, 111, and 112 are arranged are defined on the planar surface 301. For example, each area 302 may be a groove which is recessed into the planar surface 301. Each pair of light sources 110, 111, and 112 may be located in the corresponding groove. At least a part of the planar surface 301 and/or the surface of the areas 302 may be coated with a material that reflects light.

Figure 8:
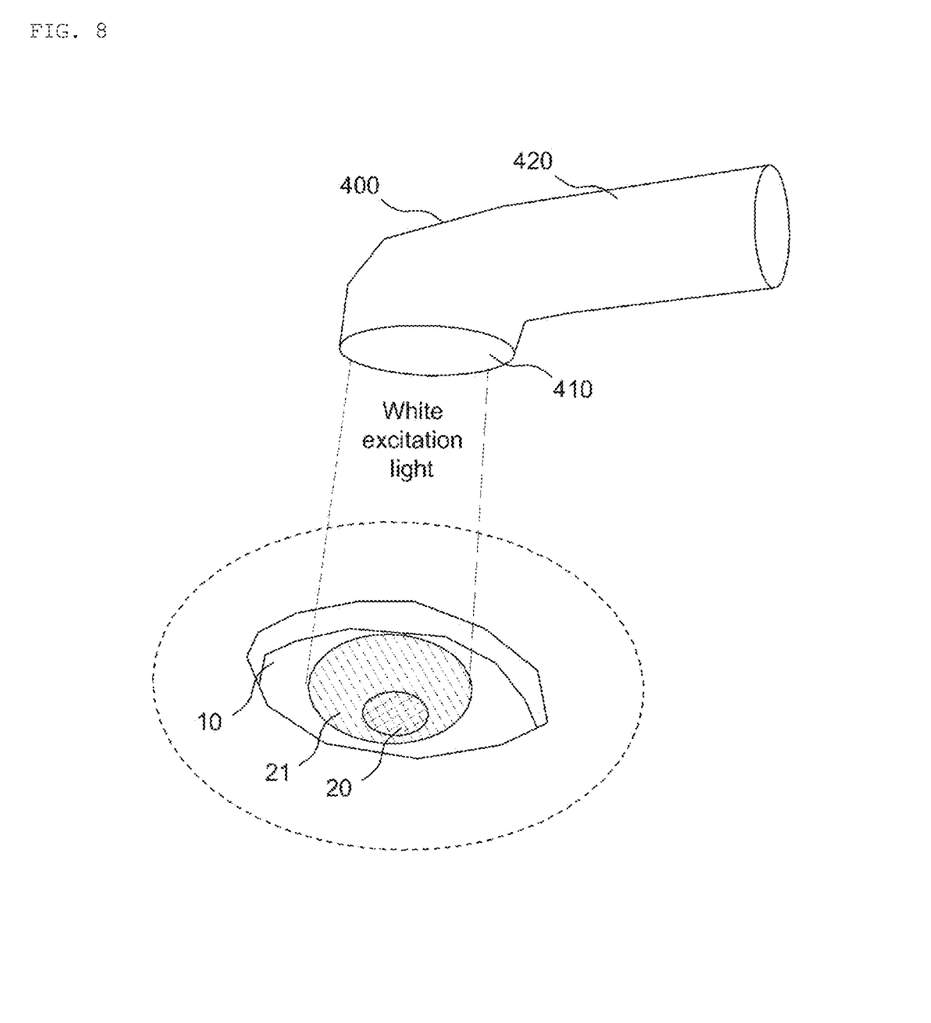
FIG. 8 is a diagram schematically illustrating a white excitation light generating device which is implemented as a hand-held type device.
Figure 9A:
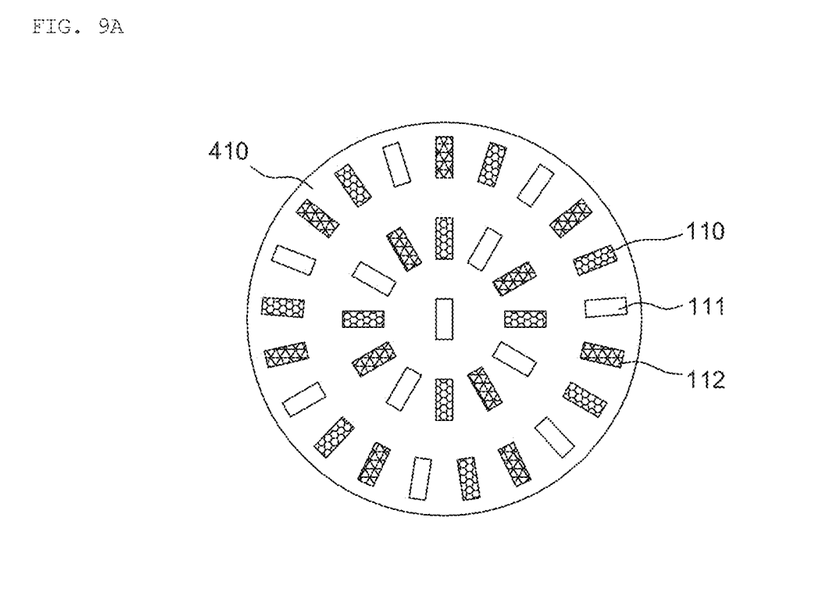
FIGS. 9A and 9B are diagrams schematically illustrating arrangements of light sources in the white excitation light generating device illustrated in FIG. 8.
Figure 9B:
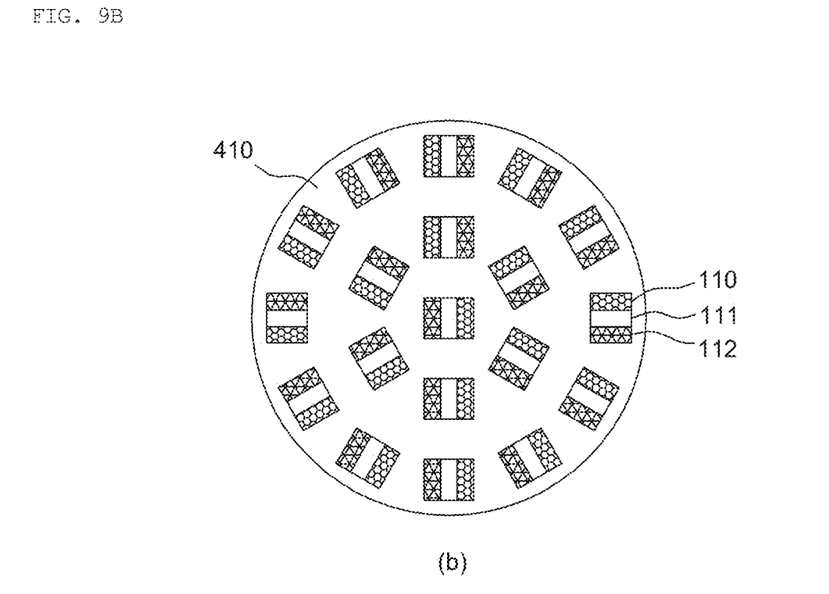

FIG. 8 is a diagram schematically illustrating a white excitation light generating device which is implemented in a hand-held type. FIGS. 9A and 9B are diagrams schematically illustrating arrangements of light sources in the white excitation light generating device illustrated in FIG. 8.

The white excitation light generating device 100 may be a hand-held device 400 which can be used by a surgeon or an assistant with a hand thereof. The hand-held device 400 can irradiate an incised portion 10 with white excitation light with better straight-travelling property than that of the operating-room illumination device 300 illustrated in FIG. 7. An area 21 in the incised portion 10 irradiated with the white excitation light is recognized in the original color. A fluorescent material included in a lesion is excited by the white excitation light and emits fluorescent light 20.

The hand-held device 400 includes a housing including an irradiation surface 410 on which light sources are arranged and a handle 420. A controller for the light sources and a power supply can be arranged in the housing. The arrangements of light sources on the irradiation surface 410 are illustrated in FIGS. 9A and 9B.

FIG. 9A illustrates light sources which are separated and arranged independently, and FIG. 9B illustrates light sources which are grouped and arranged in pairs. In FIGS. 8 to 9B, the surfaces 301 and 410 on which light sources are arranged have a circular shape. Accordingly, the light sources or the pairs of light sources 110, 111, and 112 are arranged in a radial shape. However, when the surfaces 301 and 410 on which light sources are arranged have a shape other than a circular shape, the light sources or the pairs of light sources 110, 111, and 112 may not be arranged in a radial shape.

The above description of the invention is exemplary, and those skilled in the art can understand that the invention can be modified in other forms without changing the technical concept or the essential feature of the invention. Therefore, it should be understood that the above-mentioned embodiments are exemplary in all respects, but are not definitive.

The scope of the invention is defined by the appended claims, not by the above detailed description, and it should be construed that all changes or modifications derived from the meanings and scope of the claims and equivalent concepts thereof are included in the scope of the invention.

What is claimed is:

1. A white excitation light generating device for illuminating an incised area, the white excitation light generating device comprising:
    a fluorescent excitation light source configured to generate fluorescent excitation light configured to excite a fluorescent material to emit fluorescent light;
    a first light source configured to generate first monochromatic light of a first wavelength different from a wavelength of the fluorescent excitation light;
    a second light source configured to generate second monochromatic light of a second wavelength different from the wavelength of the fluorescent excitation light and the first wavelength;
    a spectrophoto sensor configured to measure tristimulus values of at least one of the fluorescent excitation light, the first monochromatic light, and the second monochromatic light; and
    a controller configured to adjust an output of at least one of the fluorescent excitation light source, the first light source, and the second light source based at least on the measured tristimulus values,
    wherein the controller is configured to mix the first monochromatic light, the second monochromatic light, and the fluorescent excitation light to generate a white excitation light, the white excitation light configured to illuminate the incised area and to acquire a fluorescent image of the incised area based on the fluorescent light emitted by the fluorescent material.

2. The white excitation light generating device according to claim 1, wherein the controller includes a microprocessor configured to calculate chromaticity values of the fluorescent excitation light, the first monochromatic light, and the second monochromatic light using the measured tristimulus values, calculate illuminance adjustment values of the first monochromatic light and the second monochromatic light using the calculated chromaticity values, and adjust an output of at least one of the first light source and the second light source on the basis of the calculated illuminance adjustment values.

3. The white excitation light generating device according to claim 2, wherein the illuminance adjustment values of the first monochromatic light and the second monochromatic light are values for adjusting chromaticity values of the mixed light to chromaticity values of white light.

4. The white excitation light generating device according to claim 1, further comprising an illuminance sensor configured to measure an illuminance value of at least one of the fluorescent excitation light, the first monochromatic light, and the second monochromatic light,
    wherein the controller is configured to calculate chromaticity values of the fluorescent excitation light, the first monochromatic light, and the second monochromatic light using the measured tristimulus values, calculate illuminance adjustment values of the first monochromatic light and the second monochromatic light using the measured illuminance value and the calculated chromaticity values of the fluorescent excitation light, and adjust an output of at least one of the first light source and the second light source on the basis of the calculated illuminance adjustment values.

5. The white excitation light generating device according to claim 1, further comprising an illuminance sensor configured to measure an illuminance value of at least one of the fluorescent excitation light, the first monochromatic light, and the second monochromatic light,
    wherein the controller is configured to calculate chromaticity values of the fluorescent excitation light, the first monochromatic light, and the second monochromatic light using the measured tristimulus values, calculate illuminance adjustment values of the second monochromatic light and the fluorescent excitation light using the measured illuminance value and the calculated chromaticity values of the first monochromatic light, and adjust an output of at least one of the first light source and the fluorescent excitation light source on the basis of the calculated illuminance adjustment values.

6. The white excitation light generating device according to claim 1, wherein the fluorescent excitation light source, the first light source, and the second light source are narrowband LEDs, and wherein the first wavelength belongs to a blue band, the second wavelength belongs to a green band, and the wavelength of the fluorescent excitation light belongs to a near-infrared band.

7. The white excitation light generating device according to claim 1, wherein the first wavelength is 460 nm.

8. The white excitation light generating device according to claim 1, wherein the second wavelength is 540 nm.

9. The white excitation light generating device according to claim 1, wherein the wavelength of the fluorescent excitation light is 780 nm.

10. A white excitation light generating device for illuminating an incised area, the white excitation light generating device comprising:
   a fluorescent excitation light source configured to generate fluorescent excitation light configured to excite a fluorescent material to emit fluorescent light;
   a first light source configured to generate first monochromatic light of a first wavelength different from a wavelength of the fluorescent excitation light;
   a second light source configured to generate second monochromatic light of a second wavelength different from the wavelength of the fluorescent excitation light and the first wavelength;
   an illuminance sensor configured to measure an illuminance value of at least one of the fluorescent excitation light, the first monochromatic light, and the second monochromatic light; and
   a controller configured to adjust an output of at least one of the fluorescent excitation light source, the first light source, and the second light source based at least on the measured illuminance values,
   wherein the controller is configured to mix the first monochromatic light, the second monochromatic light, and the fluorescent excitation light to generate a white excitation light, the white excitation light configured to illuminate the incised area and to acquire a fluorescent image of the incised area based on the fluorescent light emitted by the fluorescent material.

11. The white excitation light generating device according to claim 10, further comprising a memory configured to store chromaticity values of the fluorescent excitation light, the first monochromatic light, and the second monochromatic light,
   wherein the controller includes a microprocessor configured to calculate the illuminance values of the first monochromatic light and the second monochromatic light using the chromaticity values of the fluorescent excitation light, the first monochromatic light, and the second monochromatic light, compare the calculated illuminance values with the measured illuminance values to calculate illuminance adjustment values, and adjust an output of the first light source and the second light source on the basis of the calculated illuminance adjustment values.

12. The white excitation light generating device according to claim 10, further comprising a memory configured to store calculated illuminance values of the fluorescent excitation light, the first monochromatic light, and the second monochromatic light which are mixed into white light,
   wherein the controller includes a microprocessor configured to compare the calculated illuminance values with the measured illuminance values to calculate illuminance adjustment values and adjust an output of the first light source and the second light source on the basis of the calculated illuminance adjustment values.

13. A method of generating white excitation light for illuminating an incised area, the method comprising:
   generating, using a fluorescent excitation light source, fluorescent excitation light configured to excite a fluorescent material to emit fluorescent light;
   generating, using a first light source, first monochromatic light of a first wavelength different from a wavelength of the fluorescent excitation light:
   generating, using a second light source, second monochromatic light of a second wavelength different from the wavelength of the fluorescent excitation light and the first wavelength;
   measuring, using a spectrophoto sensor, tristimulus values of at least one of the fluorescent excitation light, the first monochromatic light, and the second monochromatic light; and
   adjusting, using a controller, illuminance values of at least one of the fluorescent excitation light, the first monochromatic light, and the second monochromatic light on the basis of the measured tristimulus values,
   wherein the first monochromatic light, the second monochromatic light, and the fluorescent excitation light are mixed to generate a white excitation light, the white excitation light configured to illuminate the incised area and to acquire a fluorescent image of the incised area based on the fluorescent light emitted by the fluorescent material.

14. The white excitation light generating method according to claim 13, wherein adjusting the illuminance value of at least one of the fluorescent excitation light, the first monochromatic light, and the second monochromatic light on the basis of the measured tristimulus value comprises:
   calculating, using the controller, chromaticity values of the fluorescent excitation light, the first monochromatic light, and the second monochromatic light using the measured tristimulus value;
   calculating, using the controller, illuminance adjustment values of the first monochromatic light and the second monochromatic light using the calculated chromaticity values; and
   adjusting, using the controller, outputs of a first light source that generates the first monochromatic light and a second light source that generates the second monochromatic light on the basis of the calculated illuminance adjustment value.

15. The white excitation light generating method according to claim 13, further comprising measuring, using an illuminance sensor, an illuminance value of at least one of the fluorescent excitation light, the first monochromatic light, and the second monochromatic light,
   wherein adjusting the illuminance value of at least one of the fluorescent excitation light, the first monochromatic light, and the second monochromatic light on the basis of the measured tristimulus value comprises:

calculating, using the controller, chromaticity values of the fluorescent excitation light, the first monochromatic light, and the second monochromatic light using the measured tristimulus value;

calculating, using the controller, illuminance values of the first monochromatic light and the second monochromatic light using the measured illuminance value and the calculated chromaticity values of the fluorescent excitation light;

comparing, using the controller, the calculated illuminance values of the first monochromatic light and the second monochromatic light with the measured illuminance values to calculate illuminance adjustment values; and adjusting, using the controller, outputs of a first light source that generates the first monochromatic light and a second light source that generates the second monochromatic light on the basis of the calculated illuminance adjustment values.

16. The white excitation light generating method according to claim 13, further comprising measuring, using an illuminance sensor, an illuminance value of at least one of the fluorescent excitation light, the first monochromatic light, and the second monochromatic light, wherein adjusting, using the controller, the illuminance value of at least one of the fluorescent excitation light, the first monochromatic light, and the second monochromatic light on the basis of the measured tristimulus value comprising:

calculating, using the controller, chromaticity values of the fluorescent excitation light using the measured tristimulus value;

calculating, using the controller, an illuminance value of the fluorescent excitation light and the second monochromatic light using the measured illuminance value and the calculated chromaticity values of the first monochromatic light;

comparing, using the controller, the calculated illuminance values of the fluorescent excitation light and the second monochromatic light with the measured illuminance values to calculate illuminance adjustment values; and adjusting, using the controller, outputs of a fluorescent excitation light source that generates the fluorescent excitation light and a second light source that generates the second monochromatic light on the basis of the calculated illuminance adjustment values.

17. The white excitation light generating method according to claim 13, wherein the spectrophoto sensor sequentially measures of the tristimulus values of the fluorescent excitation light, the first monochromatic light, and the second monochromatic light.

18. The white excitation light generating method according to claim 13, wherein the first wavelength belongs to a blue band, the second wavelength belongs to a green band, and the wavelength of the fluorescent excitation light belongs to a near-infrared band.

* * * * *